(12) United States Patent
Lavielle et al.

(10) Patent No.: US 6,492,366 B1
(45) Date of Patent: Dec. 10, 2002

(54) CYANO-INDOLE SEROTONIN-REUPTAKE INHIBITOR COMPOUND

(75) Inventors: Gilbert Lavielle, La Celle Saint Cloud (FR); Olivier Muller, Ennery (FR); Mark Millan, Le Pecq (FR); Didier Cussac, Chatou (FR); Anne Dekeyne, Saint Remy les Chevreuses (FR)

(73) Assignee: Les Laboratoires Servier, Courbevoie (FR)

( * ) Notice: Subject to any disclaimer, the term of this patent is extended or adjusted under 35 U.S.C. 154(b) by 0 days.

(21) Appl. No.: 09/686,056

(22) Filed: Oct. 11, 2000

(30) Foreign Application Priority Data

Oct. 12, 1999 (FR) ............................................. 99 12668

(51) Int. Cl.$^7$ .................... A61K 31/495; A61K 31/405; C07D 207/08; C07D 215/00; C07D 277/62
(52) U.S. Cl. ............... 514/248; 514/252.06; 514/258.1; 514/266.2; 514/314; 514/417; 514/421; 544/235; 544/239; 544/298; 544/315; 544/316; 546/113; 546/152; 548/400; 548/152; 548/465; 548/484; 548/490; 548/492
(58) Field of Search ................................ 544/235, 315, 544/239, 298, 316; 546/113, 152; 548/452, 400, 465, 469, 484, 490, 485, 492; 514/258, 248, 252.06, 260.1, 260.2, 314, 414, 417, 421, 258.01, 266.01, 266.2, 415

(56) References Cited

FOREIGN PATENT DOCUMENTS

| EP | 610134 | * 10/1994 |
| EP | 814084 | * 12/1997 |

* cited by examiner

*Primary Examiner*—Deepak R. Rao
*Assistant Examiner*—Sudhaker B. Patel
(74) *Attorney, Agent, or Firm*—The Firm of Hueschen and Sage

(57) ABSTRACT

A compound selected from those of formula (I):

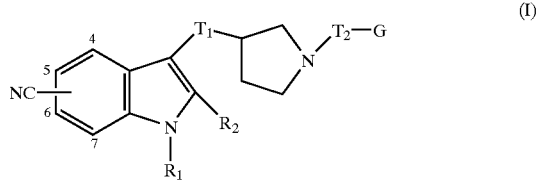

wherein:

$R_1$ and $R_2$ each independently represent hydrogen or, alkyl, $T_1$ and $T_2$ each independently represent alkylene, G represents a heterocyclic group selected of formula ($\alpha$):

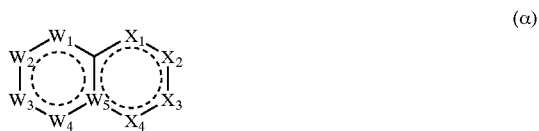

wherein:

$W_1$ to $W_5$ and $X_1$ to $X_4$ are so defined in the description.

Medicinal products containing the same are useful as serotonin-reuptake inhibitors.

13 Claims, No Drawings

CYANO-INDOLE SEROTONIN-REUPTAKE INHIBITOR COMPOUND

DESCRIPTION OF THE PRIOR ART

Compounds characterised by the combination of an indole ring system and a 2,3-dihydro-1,4-benzodioxin ring system have been described for their serotonin-reuptake inhibiting properties (WO 9717343). Indoles substituted on the aromatic moiety have also been claimed in Patent Application EP 814 084 for their action at the level of the serotonin-reuptake sites. Other compounds having related properties have been claimed in Patent Application WO 9633710 and have a benzopyran structure.

BACKGROUND OF THE INVENTION

Serotonin-reuptake inhibitors constitute a heterogeneous group of therapeutic agents. They are used in the treatment of pathologies associated with a serotonin deficit at the level of the central neurone synapses. The inhibition of serotonin reuptake by binding to transporters or presynaptic receptors is a means of restoring nerve transmission.

The use of compounds having those inhibitory properties may constitute an alternative to the use of tricyclic antidepressants or of monoamine oxidase inhibitors in the treatment of depression and associated disorders (Annals of Pharmacotherapy, 1994, 28, 1359), panic attacks and obsessive-compulsive disorders (Human Psychopharmacology, 1995, 10, 5199). The efficacy of compounds having such pharmacological properties (Journal of Psychopharmacology, 1994, 8, 238) is reinforced by the fact that they are better tolerated (International Clinical Psychopharmacology, 1995, 9 suppl. 4, 33) and are safer to use (Annals of Pharmacology, reference cited).

The compounds of the present invention are characterised by an indole ring system substituted on the benzene moiety by a cyano group and in the 3-position by an N-substituted 3-pyrrolylalkyl group. That novel structure confers upon them a powerful serotonin-reuptake inhibiting character. They will therefore be useful therapeutically in the treatment of depression, panic attacks, obsessive-compulsive disorders, phobias, impulsive disorders associated with drug abuse, bulimia nervosa and anxiety.

DETAILED DESCRIPTION OF THE INVENTION

The present invention relates to compounds of formula (I):

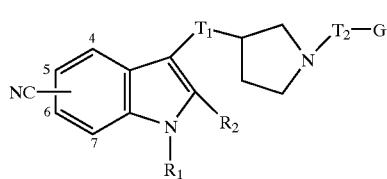

wherein:
  $R_1$ and $R_2$ each independently of the other represents a hydrogen atom or a linear or branched ($C_1$–$C_6$)alkyl group,
  $T_1$ and $T_2$ each independently of the other represents a linear or branched ($C_1$–$C_6$)-alkylene group, G represents a heterocyclic group of formula (α) or (β):

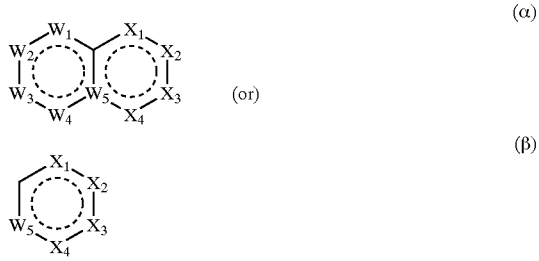

wherein:
  $W_1$ to $W_5$ and $X_1$ to $X_4$ are so selected as to form a chemically stable group and are defined as follows:
    $W_1$, $W_2$ and $W_3$ each independently of the others represents a nitrogen atom or a group $CR_5$, $NR_4$ or CO,
    $W_4$ represents a nitrogen atom or a group $CR_3$, $NR_4$ or CO,
    $W_5$ represents a carbon atom or a nitrogen atom,
    $X_1$ represents a bond, a nitrogen atom or a group $CR_3$ or $NR_4$,
    $X_2$ to $X_4$ each independently of the others represents a group $CR_3$, $NR_4$, CO, $SR_4$ or $SO_2$ or an oxygen, sulphur or nitrogen atom,
    $R_3$ represents a hydrogen or halogen atom or a linear or branched ($C_1$–$C_6$)alkyl group, hydroxy group, linear or branched ($C_1$–$C_6$)perhaloalkyl group, nitro group, or amino group (optionally substituted by one or two groups selected from linear or branched ($C_1$–$C_6$)alkyl and benzyl),
    $R_4$ represents a hydrogen atom or a linear or branched ($C_1$–$C_6$)alkyl group, optionally substituted aryl group or optionally substituted arylalkyl group,
    $R_5$ represents a group $R_3$, or two adjacent groups $R_5$ form, together with the carbon atoms carrying them, a saturated, partially unsaturated or unsaturated mono- or bi-cyclic group optionally containing from 1 to 5 hetero atoms selected from nitrogen, oxygen and sulphur, the said group being optionally substituted by one or more groups selected from $R_3$ and oxo,
  it being understood that, in formulae (α) and (β), at least one heteroatom is present, the dotted lines indicate that the groups in question may contain an unsaturated bond or a plurality of conjugated or unconjugated unsaturated bonds and that, if there is no unsaturated bond, the remaining valences are occupied by hydrogen atoms, the groups (α) and (β) being linked to $T_2$ by any one of their ring junctions,
their enantiomers and diastereoisomers, and addition salts thereof with a pharmaceutically acceptable acid or base.

Among the pharmaceutically acceptable acids there may be mentioned, by way of non-limiting examples, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, methanesulphonic acid, camphoric acid etc.

Among the pharmaceutically acceptable bases there may be mentioned, by way of non-limiting examples, sodium hydroxide, potassium hydroxide, triethylamine, tert-butylamine etc.

An aryl group is understood to mean a phenyl or naphthyl group.

The expression "optionally substituted" applied to aryl or arylalkyl groups means that the groups in question are optionally substituted by one or more groups selected from halogen atoms, linear or branched $(C_1-C_6)$alkyl groups, hydroxy groups, linear or branched $(C_1-C_6)$perhaloalkyl groups, nitro groups, and amino groups (optionally substituted by one or two groups selected from linear or branched $(C_1-C_6)$alkyl and benzyl).

Advantageously, the invention relates to compounds of formula (I) wherein the cyano group is attached in the 5-position of the indole ring system.

Another advantageous aspect of the invention relates to compounds of formula (I) wherein the cyano group is attached in the 6-position of the indole ring system.

Preferably, in the compounds of formula (I) $R_1$ and $R_2$ each represents a hydrogen atom.

Preferred compounds of the invention are those wherein $T_1$ represents a methylene group.

The preferred aryl group of the invention is the phenyl group. In preferred groups G of the invention, $R_3$, $R_4$ and $R_5$ are advantageously selected from linear or branched $(C_1-C_6)$alkyl groups, hydrogen atoms and halogen atoms.

Among preferred groups G of the invention there may be mentioned, without implying any limitation, the groups:

2-furyl; 2,4-dioxo-1,4-dihydro-3(2H)-quinazolinyl; 3-oxo-[1,2,4]triazolo[4,3-a]pyridin-2(3H)-yl; 1-oxo-2(1H)-phthalazinyl; 7-methyl-5-oxo-5H-[1,3]thiazolo[3,2-a]pyridin-6-yl; 6-chloro-2-oxo-2,3-dihydro-1H-indol-5-yl; 2-oxo-2,3-dihydro-1H-indol-5-yl; 2-oxo-1,2,3,4-tetrahydro-6-quinolinyl; 3-benzyl-5-methyl-2,6-dioxo-3,6-dihydro-1(2H)-pyrimidinyl; 1,3-dioxo-1,3-dihydro-2H-isoindol-2-yl; 1,1,3-trioxo-1,3-dihydro-2H-1,2-benzisothiazol-2-yl; 1,3-dioxo-3,6-dihydropyrrolo[3,4-c]carbazol-2(1H)-yl; 1,3-dioxo-1,3-dihydro-2H-benzo[c]isoindol-2-yl; 3,5-dimethyl-2,6-dioxo-3,6-dihydro-1(2H)-pyrimidinyl.

An especially advantageous aspect of the invention relates to compounds of formula (I) wherein $R_1$ and $R_2$ each represents a hydrogen atom, $T_1$ represents a methylene group, $T_2$ represents an alkylene group (for example methylene or ethylene) and G is selected from the groups 2-furyl; 2,4-dioxo-1,4-dihydro-3(2H)-quinazolinyl; 3-oxo-[1,2,4]triazolo-[4,3-a]pyridin-2(3H)-yl; 1-oxo-2(1H)-phthalazinyl; 7-methyl-5-oxo-5H-[1,3]thiazolo-[3,2-a]pyrimidin-6-yl; 6-chloro-2-oxo-2,3-dihydro-1H-indol-5-yl; 2-oxo-2,3-dihydro-1H- indol-5-yl; 2-oxo-1,2,3,4-tetrahydro-6-quinolinyl; 3-benzyl-5-methyl-2,6-dioxo-3,6-dihydro-1(2H)-pyrimidinyl; 1,3-dioxo-1,3-dihydro-2H-isoindol-2-yl; 1,1,3-trioxo-1,3-dihydro-2H-1,2-benzisothiazol-2-yl; 1,3-dioxo-3,6-dihydropyrrolo[3,4-c]carbazol-2(1H)-yl; 1,3-dioxo-1,3-dihydro-2H-benzo[c]isoindol-2-yl; 3,5-dimethyl-2,6-dioxo-3,6-dihydro-1(2H)-pyrimidinyl.

Among those compounds preference will be given to those wherein the cyano group is attached in the 5- or 6-position of the indole ring system, more especially those wherein the cyano group is attached in the 5-position.

Among the preferred compounds of the invention, there may be mentioned more especially:

3-({1-[2-(7-methyl-5-oxo-5H)-[1,3]thiazolo[3,2-a]pyrimidin-6-yl)ethyl]-3-pyrrolidinyl}methyl)-1H-indole-5-carbonitrile hydrochloride 3-({1-[2-(6-chloro-2-oxo-2,3-dihydro-1H-indol-5-yl)ethyl]-3-pyrrolidinyl}methyl)-1H-indole-5-carbonitrile hydrochloride.

The invention relates also to a process for the preparation of compounds of formula (I), which process is characterised in that there is used as starting material a compound of formula (II):

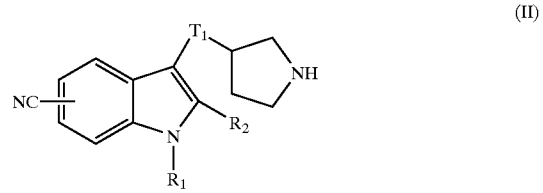

(II)

wherein $R_1$, $R_2$ and $T_1$ are as defined for formula (I), which is subjected:

either to the action, in a reducing medium, of an aldehyde of formula (III):

$$OHC-T'_2-G \quad (III)$$

wherein G is as defined for formula (I) and $T'_2$ represents a bond or a linear or branched $(C_1-C_5)$alkylene group, or to the action, in a basic medium, of a halogenated compound of formula (IV):

$$Hal-T_2-G \quad (IV)$$

wherein $T_2$ is as defined for formula (I) and Hal represents a halogen atom, to yield a compound of formula (I), or which is subjected to the action, in a basic medium, of a compound of formula (V):

$$Hal-T_2-NH-P' \quad (V)$$

wherein $T_2$ is as defined for formula (I), Hal represents a halogen atom and P' is a protecting group for the amine, to yield a compound of formula (VI),

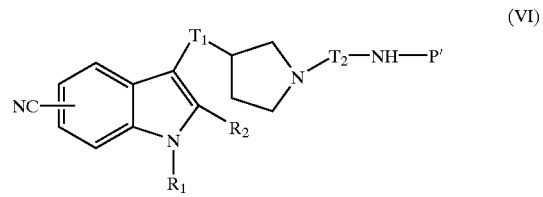

(VI)

wherein $R_1$, $R_2$, $T_1$, $T_2$ and P' are as defined hereinbefore, which compound of formula (VI), after deprotection of the primary amine group, is condensed with a cyclic group that is a precursor of group G defined for formula (I) to yield a compound of formula (I/a):

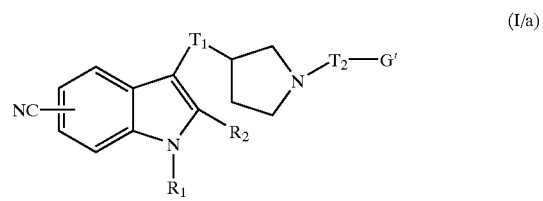

(I/a)

a particular case of the compounds of formula (I) wherein $R_1$, $R_2$, $T_1$ and $T_2$ are as defined hereinbefore and G' represents a group as defined for G in formula (I), it being understood that G' is attached to $T_2$ by a nitrogen atom, which compounds of formulae (I/a) and (I), may be purified, if necessary, according to a conventional purification technique, are separated, where appropriate, into their isomers according to a conventional separation technique, are converted, if desired, into addition salts thereof with a pharmaceutically acceptable acid or base.

The present invention relates also to pharmaceutical compositions comprising as active ingredient at least one compound of formula (I), alone or in combination with one or more inert, non-toxic pharmaceutically acceptable excipients or carriers.

Among the pharmaceutical compositions according to the invention there may be mentioned more especially those that are suitable for oral, parenteral or nasal administration, tablets or dragees, sublingual tablets, gelatin capsules, lozenges, suppositories, creams, ointments, dermal gels etc.

The useful dosage varies according to the age and weight of the patient, the nature and severity of the disorder and the route of administration, which may be oral, nasal, rectal or parenteral. The unit dose generally ranges from 0.1 to 500 mg for a treatment in from 1 to 3 administrations per 24 hours.

The following Examples illustrate the invention and do not limit it in any way.

The starting materials used are known products or are prepared according to known procedures.

Preparation A: 3-[(3-Pyrrolidinyl)methyl]-1H-indole-5-carbonitrile

Hydrogenolysis of 0.32 mol (96 g) of 3-(1-benzyl-3-pyrrolidinylmethyl)-1H-indole-5-carbonitrile (described in Patent Application EP 610 134) is carried out in 1.7 liters of ethanol in the presence of 9.6 g of carbon containing 20% palladium hydroxide moist (Pearlman's catalyst) and 0.32 mol of hydrochloric acid in ethanol at 70° C. and at atmospheric pressure. After absorption of the theoretical amount of hydrogen, the catalyst is filtered off and the filtrate is then concentrated. The base is precipitated out by 1N sodium hydroxide solution and extracted using dichloromethane to yield the expected product.

Preparation B: tert-Butyl 2-bromoethylcarbamate

Under an inert atmosphere and at ambient temperature, a solution of 62 mmol (10 g) of N-(tert-butoxycarbonyl) ethanolamine in 100 ml of acetonitrile is prepared, to which 74.5 mmol (24.7 g) of tetrabromomethane are added. 68.2 mmol (17.9 g) of triphenyl-phosphine dissolved in 150 ml of acetonitrile are then added dropwise. The reaction mixture is stirred at ambient temperature for 30 minutes and is then concentrated. The residue is taken up in isopropyl ether and, after filtration, the filtrate is concentrated to obtain the title product.

EXAMPLE 1

3-{[1-(2-Furylmethyl)-3-pyrrolidinyl]methyl}-1H-indole-5-carbonitrile Oxalate

Under an inert atmosphere and at ambient temperature, 47.3 mmol (10 g) of 3-[3-pyrrolidinylmethyl]-1H-indole-5-carbonitrile (described in Preparation A) are dissolved in 650 ml of 1,2-dichloroethane, and then 47.3 mmol (4.26 g) of furaldehyde are added. Stirring is carried out for 10 minutes, and 66.2 mmol (13.79 g) of sodium triacetoxyborohydride are added. After 30 minutes at ambient temperature, 350 ml of saturated sodium hydrogen carbonate solution are added. The organic phase is separated off, washed with water and dried over magnesium sulphate. Purification is carried out by chromatography on silica using a mixture of dichloromethane/methanol/ammonia 98/2/0.2 as eluant. The compound obtained is converted into the salt by one equivalent of oxalic acid in ethanol.

Melting point: 120–122° C.

Elemental microanalysis.

|  | C | H | N |
|---|---|---|---|
| % calculated | 63.79 | 5.35 | 10.63 |
| % found | 63.54 | 5.58 | 10.37 |

EXAMPLE 2

3-[(1-{2-[2,4-Dioxo-1,4-dihydro-3(2H)-quinazolinyl]ethyl}-3-pyrrolidinyl)methyl]-1H-indole-5-carbonitrile Hydrochloride Under an inert atmosphere and at ambient temperature, 47.3 mmol (10 g) of 3-[3-pyrrolidinylmethyl]-1H-indole-5-carbonitrile, 47.3 mmol (9.97 g) of 3-(2-chloroethyl)-2,4-(1H,3H)-quinazolinedione and 47.3 mmol (3.73 g) of sodium hydrogen carbonate are dissolved in 100 ml of dimethylformamide, and stirring is carried out at 100° C. for 6 hours. The reaction mixture is concentrated and the residue is taken up in dichloromethane. The organic phase is washed with water and then with saturated sodium chloride solution, and is dried over magnesium sulphate. Purification is carried out by chromatography on silica using a mixture of dichloromethane/methanol/ammonia 95/5/0.5 as eluant. The compound obtained is converted into the salt by one equivalent of hydrochloric acid in ethanol.

Melting point: 152–154° C.

Elemental microanalysis:

|  | C | H | N | Cl |
|---|---|---|---|---|
| % calculated | 64.07 | 5.38 | 15.57 | 7.88 |
| % found | 63.81 | 5.34 | 15.20 | 7.64 |

EXAMPLE 3

3-[(1-{2-[3-Oxo-[1,2,4]triazolo[4,3-a]pyridin-2(3H)-yl]ethyl}-3-pyrrolidinyl)methyl]-1H-indole-5-carbonitrile Hydrochloride The expected product is obtained according to the procedure described in Example 2, replacing the 3-(2-chloroethyl)-2,4-(1H,3H)-quinazolinedione by 2-(2-chloroethyl)-[1,2,4]triazolo[4,3-a]pyridin-3(2H)-one.

Melting point. 140° C.

Elemental microanalysis:

|  | C | H | N | Cl |
|---|---|---|---|---|
| % calculated | 62.48 | 5.48 | 19.87 | 8.38 |

|  | C | H | N | Cl |
|---|---|---|---|---|
| % found | 62.48 | 5.68 | 19.54 | 8.48 |

EXAMPLE 4

3-[(1-{2-[1-Oxo-2(1H)-phthalazinyl]ethyl}-3-pyrrolidinyl)methyl]-1H-indole-5-carbonitrile Hydrochloride The expected product is obtained according to the procedure described in Example 2, replacing the 3-(2-chloroethyl)-2,4-(1H,3H)-quinazolinedione by 2-(2-chloroethyl)-1(2H)-phthalazinone.

Melting point: 125–127° C.

Elemental microanalysis:

|  | C | H | N | Cl |
|---|---|---|---|---|
| % calculated | 66.43 | 5.57 | 16.14 | 8.17 |
| % found | 66.74 | 5.63 | 15.79 | 8.27 |

EXAMPLE 5

3-({1-[2-(7-Methyl-5-oxo-(5H)-[1,3]thiazolo[3,2-a]pyrimidin-6-yl)-ethyl]-3-pyrrolidinyl}methyl)-1H-indole-5-carbonitrile Hydrochloride The expected product is obtained according to the procedure described in Example 2, replacing the 3-(2-chloroethyl)-2,4-(1H,3H)-quinazolinedione by 6-(2-chloroethyl)-7-methyl-5H-[1,3]thiazolo[3,2-a]pyrimidin-5-one.

Melting point: 234–236° C.

Elemental microanalysis:

|  | C | H | N | S | Cl |
|---|---|---|---|---|---|
| % calculated | 60.85 | 5.33 | 15.43 | 7.06 | 7.81 |
| % found | 59.83 | 5.38 | 14.69 | 6.90 | 7.69 |

EXAMPLE 6

3-({1-[2-(6-Chloro-2-oxo-2,3-dihydro-1H-indol-5-yl)ethyl]-3-pyrrolidinyl}methyl)-1H-indole-5-carbonitrile Hydrochloride The expected product is obtained according to the procedure described in Example 2, replacing the 3-(2-chloroethyl)-2,4-(1H,3H)-quinazolinedione by 6-chloro-5-(2-chloroethyl)-1,3-dihydro-2H-indol-2-one.

Melting point: 115–117° C.

Elemental microanalysis:

|  | C | H | N | Cl |
|---|---|---|---|---|
| % calculated | 63.30 | 5.31 | 12.30 | 15.57 |

|  | C | H | N | Cl |
|---|---|---|---|---|
| % found | 63.57 | 5.42 | 12.06 | 15.27 |

EXAMPLE 7

3-({1-[2-(2-Oxo-2,3-dihydro-1H-indol-5-yl)ethyl]-3-pyrrolidinyl}-methyl)-1H-indole-5-carbonitrile Hydrochloride The expected product is obtained according to the procedure described in Example 2, replacing the 3-(2-chloroethyl)-2,4-(1H,3H)-quinazolinedione by 5-(2-chloroethyl)-1,3-dihydro-2H-indol-2-one.

Melting point: 118–120° C.

Elemental microanalysis:

|  | C | H | N | Cl |
|---|---|---|---|---|
| % calculated | 68.48 | 5.99 | 13.31 | 8.42 |
| % found | 68.85 | 6.30 | 12.81 | 8.50 |

EXAMPLE 8

3-({1-[2-(2-Oxo-1,2,3,4-tetrahydro-6-quinolinyl)ethyl]-3-pyrrolidinyl}methyl)-1H-indole-5-carbonitrile Hydrochloride The expected product is obtained according to the procedure described in Example 2, replacing the 3-(2-chloroethyl)-2,4-(1H,3H)-quinazolinedione by 6-(2-bromoethyl)-3,4-dihydro-2(1H)-quinolinone.

Melting point: 110° C. (dec.)

Elemental microanalysis:

|  | C | H | N | Cl |
|---|---|---|---|---|
| % calculated | 69.03 | 6.26 | 12.88 | 8.15 |
| % found | 69.10 | 6.40 | 12.31 | 8.19 |

EXAMPLE 9

3-[(1-{2-[3-Benzyl-5-methyl-2,6-dioxo-3,6-dihydro-1(2H)-pyrimidinyl]ethyl}-3-pyrrolidinyl)methyl]-1H-indole-5-carbonitrile The expected product is obtained according to the procedure described in Example 2, replacing the 3-(2-chloroethyl)-2,4-(1H,3H)-quinazolinedione by 1-benzyl-3-(2-chloroethyl)-5-methyl-2,4-(1H,3H)-pyrimidinedione.

Melting point: 130–132° C.

Elemental microanalysis:

|  | C | H | N | Cl |
|---|---|---|---|---|
| % calculated | 66.72 | 6.00 | 13.89 | 7.03 |

|  | C | H | N | Cl |
|---|---|---|---|---|
| % found | 66.49 | 6.12 | 13.38 | 6.99 |

EXAMPLE 10

3-({1-[2-(1,3-Dioxo-1,3-dihydro-2H-isoindol-2-yl) ethyl]-3-pyrrolidinyl}methyl)-1H-indole-5-carbonitrile Hydrochloride

Step 1: tert-Butyl 2-{3-[(5-cyano-1H-indol-3-yl)methyl]-1-pyrrolidinyl}ethyl-carbamate Under an inert atmosphere, 47.3 mmol (10 g) of 3-[(3-pyrrolidinyl)methyl]-1H-indole-5-carbonitrile, 47.3 mmol (9.95 g) of the product described in Preparation B and 1.55 ml of 2-butanone are mixed together and then 47.3 mmol (4.45 g) of potassium hydrogen carbonate are added. The mixture is stirred at 80° C. for 2 hours. After hydrolysis and separating off, the organic phase is washed with saturated sodium chloride solution, dried over magnesium sulphate, filtered and concentrated. Purification is carried out by chromatography on silica, using a mixture of dichloromethane/methanol/ammonia 97/3/0.3 as eluant, to yield the expected product.

Step 2: 3-{[1-(2-Aminoethyl)-3-pyrrolidinyl]methyl}-1H-indole-5-carbonitrile At ambient temperature, 44.4 mmol (5 g) of the product described in the previous Step are dissolved in a mixture of 150 ml of 3N hydrochloric acid and 100 ml of ethyl acetate. The mixture is stirred at that temperature for 30 minutes. After separating the two phases, the acid phase is concentrated. The residue is taken up in 0.1N sodium hydroxide solution and is then extracted with dichloromethane. The organic phase is washed with water and then with saturated sodium chloride solution, and is dried over magnesium sulphate, filtered and concentrated to obtain the title product.

Step 3: 3-({1-[2-(1,3-Dioxo-1,3-dihydro-2H-isoindol-2-yl)ethyl]-3-pyrrolidinyl}methyl)-1H-indole-5-carbonitrile Hydrochloride 11.2 mmol (3 g) of the product obtained in the previous Step, 12.3 mmol (1.82 g) of phthalic anhydride and then 28 ml of glacial acetic acid are mixed together in succession. The reaction mixture is heated at reflux for 1 hour, and the acetic acid is then evaporated off. The residue is taken up in 1N sodium hydroxide solution and is extracted with dichloromethane. The organic phase is washed with water and then with saturated sodium chloride solution, and is dried over magnesium sulphate, filtered and concentrated. Purification is carried out by chromatography on silica, using a mixture of dichloromethane/methanol/ammonia 97/3/0.3 as eluant. The product obtained is converted into the salt by one equivalent of hydrochloric acid in ethanol.

Melting point: 140–142° C.

Elemental microanalysis:

|  | C | H | N | Cl |
|---|---|---|---|---|
| % calculated | 66.28 | 5.33 | 12.88 | 8.15 |
| % found | 65.68 | 5.42 | 12.30 | 8.32 |

EXAMPLE 11

3-({1-[2-(1,1,3-Trioxo-1,3-dihydro-2H-1,2-benzisothiazol-2-yl)-ethyl]-3-pyrrolidinyl}methyl)-1H-indole-5-carbonitrile Hydrochloride The expected product is obtained according to the procedure described in Example 10, replacing the phthalic anhydride by methyl 2-chlorosulphonylbenzoate.

EXAMPLE 12

3-({1-[2-(1,3-Dioxo-1,3-dihydro-2H-benzo[e]isoindol-2-yl)ethyl]-3-pyrrolidinyl}methyl)-1H-indole-5-carbonitrile Hydrochloride The expected product is obtained according to the procedure described in Example 10, replacing the phthalic anhydride by naphtho[1,2-c]furan-1,3-dione.

Melting point: 112–116° C.

Elemental microanalysis:

|  | C | H | N | Cl |
|---|---|---|---|---|
| % calculated | 69.34 | 5.20 | 11.55 | 7.31 |
| % found | 68.58 | 5.49 | 11.10 | 6.90 |

EXAMPLE 13

3-[(1-{2-[6-Methyl-1,3-dioxo-3,6-dihydropyrrolo[3,4-c]carbazol-2(1H)-yl]ethyl}-3-pyrrolidinyl)methyl]-1H-indole-5-carbonitrile Hydrochloride The expected product is obtained according to the procedure described in Example 10, replacing the phthalic anhydride by 1H-furo[3,4-c]carbazole-1,3(6H)-dione.

Melting point: 210–215° C.

Elemental microanalysis:

|  | C | H | N | Cl |
|---|---|---|---|---|
| % calculated | 69.20 | 5.25 | 13.02 | 6.59 |
| % found | 68.70 | 5.21 | 12.65 | 6.87 |

EXAMPLE 14

3-({1-[2-(3,5-Dimethyl-2,6-dioxo-3,6-dihydro-1(2H)-pyrimidinyl)ethyl]-3-pyrrolidinyl}-methyl)-1H-indole-5-carbonitrile Hydrochloride The expected product is obtained according to the procedure described in Example 2, replacing the 3-(2-chloroethyl)-2,4-(1H,3H)-quinazolinedione by 3-(2-chloroethyl)-1,5-dimethyl-2,4-(1H,3H)-pyrimidinedione.

Elemental microanalysis:

|  | C | H | N | Cl |
|---|---|---|---|---|
| % calculated | 61.75 | 6.12 | 16.37 | 8.28 |
| % found | 61.31 | 6.54 | 15.94 | 8.08 |

The following compounds are obtained in the same manner:

EXAMPLE 15

3-[(1-{2-[2,4-Dioxo-1,4-dihydro-3(2H)-quinazolinyl]ethyl}-3-pyrrolidinyl)methyl]-1H-indole-6-carbonitrile Hydrochloride

EXAMPLE 16

3-({1-[2-(7-Methyl-5-oxo-(5H)-[1,3]thiazolo[3,2-a]pyrimidin-6-yl)-ethyl]-3-pyrrolidinyl}methyl)-1H-indole-6-carbonitrile Hydrochloride

EXAMPLE 17

3-({1-[2-(6-Chloro-2-oxo-2,3-dihydro-1H-indol-5-yl)ethyl]-3-pyrrolidinyl}methyl)-1H-indole-6-carbonitrile Hydrochloride

EXAMPLE 18

3-({1-[2-(1,3-Dioxo-1,3-dihydro-2H-isoindol-2-yl)ethyl]-3-pyrrolidinyl}methyl)-1H-indole-6-carbonitrile Hydrochloride

EXAMPLE 19

3-[(1-{2-[6-Methyl-1,3-dioxo-3,6-dihydropyrrolo[3,4-c]carbazol-2(1H)-yl]ethyl}-3-pyrrolidinyl)methyl]-1H-indole-6-carbonitrile Hydrochloride

EXAMPLE 20

3-({1-[2-(3,5-Dimethyl-2,6-dioxo-3,6-dihydro-1(2H)-pyrimidinyl)ethyl]-3-pyrrolidinyl}methyl)-1H-indole-6-carbonitrile Hydrochloride Pharmacological Study

EXAMPLE A

Determination of Affinity for Serotonin-reuptake Sites in the Rat

The affinity of the compounds of the invention was determined by competition experiments with [³H]-paroxetine. The membranes are prepared from rat frontal cortex and are incubated in triplicate with 0.25 nM [³H]-paroxetine and the cold ligand in a final volume of 0.4 ml, for 2 hours at 25° C. The incubation buffer contains 50 mM TRIS-HCl (pH 7.4), 120 mM NaCl and 5 mM KCl. Non-specific binding is determined using 10 μM citalopram. At the end of the incubation, the mixture is filtered through filters and washed three times with 5 ml of cooled buffer. The radioactivity retained on the filters is determined by liquid scintillation counting. The binding isotherms are analysed by non-linear regression to determine the IC$_{50}$ values. The latter are converted into a dissociation constant (K$_i$) using the Cheng-Prusoff equation:

$$K_i = IC_{50}/\{(L/K_d)-1\}$$

wherein L is the concentration of [³H]-paroxetine and K$_d$ is the dissociation constant (0.13 nM).

The compounds of the invention appear to have a very high affinity for serotonin-reuptake sites.

By way of example, the affinity of the compound of Example 6 is 4·10$^{-10}$M.

EXAMPLE B

Marble-burying Test in Mice

This test enables evaluation of the capacity of pharmacological agents to inhibit the spontaneous marble-burying behaviour of mice, the inhibition being predictive of anti-depressant and/or anti-impulsive action. Male mice of the NMRI strain weighing from 20 to 25 g on the day of the experiment are placed individually in Macrolon boxes (30× 18×19 cm) containing 5 cm of sawdust and covered with a perforated plexiglass plate. Twenty four "tiger's eye" glass marbles are evenly distributed on the sawdust at the periphery of the box. At the end of 30 minutes' free exploration, the animals are removed from the box and the number of buried marbles is counted.

Results: It appears that compounds of the invention inhibit the spontaneous marble-burying behaviour of mice. By way of example, compounds of examples 6 and 7 possess an ED$_{50}$ (Efficacy dose 50) of 3.8 mg/kg and 1.5 mg/kg, respectively.

EXAMPLE C

Pharmaceutical Composition

Formulation for the preparation of 1000 tablets each containing 10 mg of active ingredient:
Compound of example 6 10 g
Hydroxypropyl cellulose 2 g
Wheat starch 10 g
Lactose 100 g
Magnesium stearate 3 g
Talc 3 g

What is claimed is:

1. A compound selected from those of formula (I):

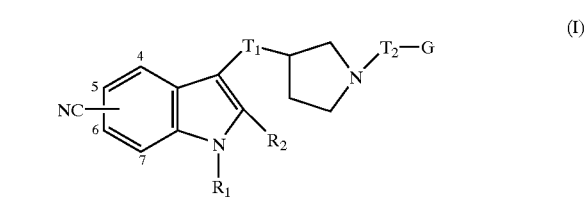

(I)

wherein:
R$_1$ and R$_2$ each independently represent hydrogen, or linear or branched (C$_1$–C$_6$)alkyl,
T$_1$ and T$_2$ each independently represent linear or branched (C$_1$–C$_6$)alkylene,
G represents a heterocyclic group selected from those of formula (α):

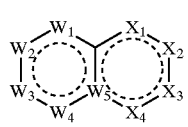

(α)

wherein:
W$_1$ to W$_5$ and X$_1$ to X$_4$ are defined as follows:
W$_1$, W$_2$ and W$_3$ each independently represent nitrogen, CR$_5$, NR$_4$, or CO, W$_4$ represents nitrogen, CR$_3$, NR$_4$ or CO,
W$_5$ represents carbon or nitrogen,
X$_1$ represents a bond, or CR$_3$,
X$_2$ to X$_4$ each independently represent CR$_3$, NR$_4$, CO, SR$_4$, SO$_2$ oxygen, sulphur, or nitrogen,
R$_3$ represents hydrogen, halogen, linear or branched (C$_1$–C$_6$)alkyl, hydroxy, linear or branched (C$_1$–C$_6$)perhaloalkyl, nitro, or amino optionally substituted by one or two groups selected from linear or branched (C$_1$–C$_6$)alkyl, benzyl,
R$_4$ represents hydrogen, linear or branched (C$_1$–C$_6$) alkyl, optionally substituted aryl, or optionally substituted arylalkyl,
R$_5$ represents R$_3$, or two adjacent groups R$_5$ form, together with the carbon atoms carrying them, a saturated, partially unsaturated or unsaturated mono- or bi-cyclic group optionally containing 1 to 5 hetero atoms selected from nitrogen, oxygen and sulphur, said group being optionally substituted by one or more groups selected from R$_3$ or oxo, it being understood that, in formulae (α) and (β), at least one heteroatom is present, the dotted lines indicate that the groups in question may contain an unsaturated bond or a plurality of conjugated or unconjugated unsaturated bonds and that, if there is no unsaturated bond, the remaining valences are occupied by hydrogen atoms, the groups (α) and (β) being linked to T$_2$ by any one of their ring junctions, its enantiomers, diastereoisomers, or addition salts thereof with a pharmaceutically-acceptable acid or base.

2. A compound of claim 1, wherein the cyano group is attached in the 5-position of the indole ring system.

3. A compound of claim 1, wherein the cyano group is attached in the 6-position of the indole ring system.

4. A compound of claim 1, wherein R$_1$ and R$_2$ each represents hydrogen.

5. A compound of formula (I) according to claim 1, wherein T$_1$ represents methylene.

6. A compound of claim 1, wherein G is selected from the group consisting of: 2-furyl; 2,4-dioxo-1,4-dihydro-3(2H)-quinazolinyl; 3-oxo-[1,2,4]triazolo[4,3-a]-pyridin-2(3H)-yl; 1-oxo-2(1H)-phthalazinyl; 7-methyl-5-oxo-5H-[1,3]thiazolo-[3,2-a]pyrimidin-6-yl; 6-chloro-2-oxo-2,3dihydro-1H-indol-5-yl; 2-oxo-2,3-dihydro-1H-indol-5-yl; 2-oxo-1,2,3,4-tetrahydro-6-quinolinyl; 3-benzyl-5-methyl-2,6dioxo-3,6-dihydro-1(2H)-pyrimidinyl; 1,3-dioxo-1,3-dihydro-2H-isoindol-2-yl; 1,1,3-trioxo-1,3-dihydro-2H-1,2-benzisothiazol-2-yl; 1,3-dioxo-3,6dihydropyrrolo-3,4-c]carbazol-2(1H)-yl; 1,3dioxo-1,3-dihydro-2H-benzo[c]isoindol-2-yl; and 3,5-dimethyl-2,6-dioxo-3,6-dihydro-1(2H)-pyrimidinyl, its enantiomers, diastereoisomers, or addition salts thereof with a pharmaceutically acceptable acid or base.

7. A compound of claim 1, wherein R$_1$ and R$_2$ each represents hydrogen, T$_1$ represents methylene, T$_2$ represents alkylene and G is selected from the group consisting of 2-furyl; 2,4dioxo-1,4-dihydro-3(2H)-quinazolinyl; 3oxo-[1,2,4]triazolo[4,3-a]pyridin-2(3H)-yl; 1-oxo-2(1H)-phthalazinyl; 7-methyl-5-oxo-5H-[1,3]thiazolo[3,2-a]pyrimidin-6-yl; 6chloro-2-oxo-2,3-dihydro-1H-indol-5-yl; 2-oxo-2,3dihydro-1H-indol-5-yl; 2-oxo-1,2,3,4-tetrahydro-6-quinolinyl; 3-benzyl-5-methyl-2,6-dioxo-3,6dihydro-1(2H)-pyrimidinyl; 1,3-dioxo-1,3-dihydro-2H-isoindol-2-yl; 1,1,3-trioxo-1,3-dihydro-2H-1,2-benzisothiazol-2-yl; 1,3-dioxo-3,6-dihydropyrrolo[3,4-c]carbazol-2(1H)-yl; 1,3dioxo-1,3-dihydro-2H-benzo[c]isoindol-2-yl; and 3,5-dimethyl-2,6dioxo-3,6-dihydro-1(2H)-pyrimidinyl, its enantiomers, diastereoisomers, or addition salts thereof with a pharmaceutically acceptable acid or base.

8. A compound of claim 7, wherein the cyano group is attached in the 5-position of the indole ring system.

9. A compound of claim 7, wherein the cyano group is attached in the 6-position of the indole ring system.

10. A compound of claim 1 which is:
3-({1-[2-(7-methyl-5-oxo-5H)-[1,3]thiazolo[3,2-a]pyrimidin-6-yl)ethyl]-3-pyrrolidinyl}methyl)-1H-indole-5-carbonitrile hydrochloride.

11. A compound of claim 1 which is:
3-({1-[2-(6-chloro-2-oxo-2,3-dihydro-1H-indol-5-yl)ethyl]-3-pyrrolidinyl}-methyl)-1H-indole-5-carbonitrile hydrochloride.

12. A pharmaceutical composition useful as a serotonin-reuptake inhibitor comprising as active principle an effective amount of a compound of claim 1 together with one or more pharmaceutically-acceptable excipients or vehicles.

13. A method for treating a living animal body afflicted with a condition or disorder requiring a serotonin-reuptake inhibitor, comprising the step of administering to the living body an amount of a compound of claim 1 which is effective for alleviation of said condition or disorder.

* * * * *